(12) United States Patent
Brookfield et al.

(10) Patent No.: US 7,939,532 B2
(45) Date of Patent: May 10, 2011

(54) HETEROCYCLYL PYRIDYL SULFONAMIDE DERIVATIVES, THEIR MANUFACTURE AND USE AS PHARMACEUTICAL AGENTS

(75) Inventors: Frederick Brookfield, Benson (GB); Jonathan Gridley, Reading (GB); Lothar Kling, Mannheim (DE); Michael Prime, Oxon (GB); Ulrike Reiff, Penzberg (DE); Wolfgang Von Der Saal, Murnau (DE); Thomas Von Hirschheydt, Penzberg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 263 days.

(21) Appl. No.: 12/377,911

(22) PCT Filed: Oct. 24, 2006

(86) PCT No.: PCT/EP2007/009238
§ 371 (c)(1),
(2), (4) Date: Feb. 18, 2009

(87) PCT Pub. No.: WO2008/049605
PCT Pub. Date: May 2, 2008

(65) Prior Publication Data
US 2010/0292247 A1   Nov. 18, 2010

(30) Foreign Application Priority Data

Oct. 26, 2006   (EP) .................................. 06022365

(51) Int. Cl.
*A61K 31/438* (2006.01)
*A61K 31/4545* (2006.01)
*A61K 31/496* (2006.01)
*C07D 213/74* (2006.01)
*C07D 401/12* (2006.01)
*C07D 491/13* (2006.01)
*A61P 35/00* (2006.01)

(52) U.S. Cl. .................... 514/253.12; 514/278; 514/318; 544/360; 544/365; 546/19; 546/194

(58) Field of Classification Search ........................ None
See application file for complete search history.

(56) References Cited

U.S. PATENT DOCUMENTS

| 4,018,929 A | 4/1977 | Delarge et al. |
| 7,625,896 B2 * | 12/2009 | Kling et al. ............... 514/237.2 |

FOREIGN PATENT DOCUMENTS

| WO | WO 02/098848 | 12/2002 |
| WO | WO 03/029217 | 4/2003 |
| WO | WO 03/035629 | 5/2003 |
| WO | WO 2004/048329 | 6/2004 |
| WO | WO 2008/049605 | 5/2008 |

OTHER PUBLICATIONS

Delarge et al., Ann. Pharm. Fr. 41, 1983, pp. 55-60.
Owa et al., Bioorg. Med. Chem. Lett. vol. 12, 2002, pp. 2097-2100.
Petros A. M., J. of Med. Chem. vol. 49, 2006, pp. 656-663.

* cited by examiner

*Primary Examiner* — Emily Bernhardt
(74) *Attorney, Agent, or Firm* — George W. Johnston; Patricia S. Rocha-Tramaloni; David E. Wildman

(57) ABSTRACT

Objects of the present invention are the compounds of formula I, their pharmaceutically acceptable salts, enantiomeric forms, diastereoisomers and racemates, the preparation of the above compounds, medicaments containing them and their manufacture, as well as the use of the above compounds in the control or prevention of illnesses such as cancer.

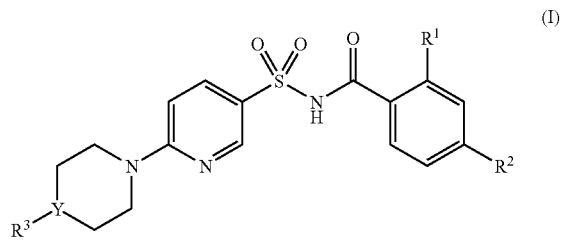

(I)

7 Claims, No Drawings

HETEROCYCLYL PYRIDYL SULFONAMIDE DERIVATIVES, THEIR MANUFACTURE AND USE AS PHARMACEUTICAL AGENTS

This application claims the benefit of European Application No. 06022365.8, filed Oct. 26, 2006. The entire contents of the above-identified application are hereby incorporated by reference.

The present invention relates to novel heterocyclyl pyridyl sulfonamide derivatives, to a process for their manufacture, pharmaceutical compositions containing them and their manufacture as well as the use of these compounds as pharmaceutically active agents.

BACKGROUND OF THE INVENTION

The treatment of cancer diseases is of great importance in medicine. There is a worldwide need for effective cancer therapies in order to achieve a treatment which is appropriate to a patient and is target-orientated. This can be seen in the large number of scientific studies which have recently appeared in the fields of applied oncology and fundamental research relating to cancer therapy.

The effects of tumor inhibitors are due to a very wide variety of mechanisms, only some of which are known. It is not unusual for known tumor drugs to be found to have new mechanisms of action. This is also to be expected in the case of the compounds according to the invention. Many tumor drugs act by way of mechanisms such as blockading the mechanism of cell division in the cell, preventing the tumor from being supplied with nutrients and oxygen (antiangiogenesis), preventing metastasis, preventing the reception and the onward transmission of growth signals to the tumor cell or forcing the tumor cell into programmed cell death (apoptosis).

Because they have different mechanisms of action, including interacting with different intracellular targets, the clinically relevant cytostatic agents are frequently administered in combination in order to achieve a synergistic therapeutic effect.

Delarge, J. and Ghys, A., Ann. Pharm. Fr. 41 (1983) 55-60, describes some 4-phenylthiopyridine-3-sulfonamides with hypolipemic properties. U.S. Pat. No. 4,018,929 relates to pyridinesulfonamides as inflammation inhibitors and diuretics. Owa, T., et al., Bioorg. Med. Chem. Lett. 12 (2002) 2097-2100 relates to N-(7-indolyl)-3-pyridinesulfonamide derivatives as antitumor agents.

WO 2003/035629 relates to thiophene- and thiazole-sulfonamides as antineoplastic agents. WO 02/098848 and WO 2004/048329 relate to benzoylsulfonamides as antitumor agents.

SUMMARY OF THE INVENTION

The present invention relates to heterocyclyl pyridyl sulfonamides of the general formula I

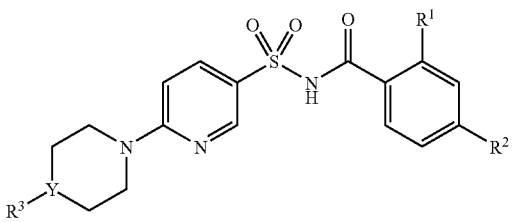

formula I wherein
$R^1$ is fluorine, chlorine, bromine, methyl, methoxy or trifluoromethyl;
$R^2$ is fluorine, chlorine, bromine, methyl or trifluoromethyl;
Y is N or CH;
$R^3$ is a) phenyl, unsubstituted or substituted one to three times by alkyl, —OR, —NRR', halogen, —CN, —CF$_3$, —OCF$_3$, —CHF$_2$ or —OCHF$_2$,
b) pyridyl, unsubstituted or substituted one to three times by alkyl; or
c) heterocyclyl, unsubstituted or substituted one to three times by alkyl;
R is hydrogen or alkyl;
and all pharmaceutically acceptable salts thereof.

The compounds according to this invention show antiproliferative activity and inhibit the growth of tumor cells in vitro and in vivo. Objects of the present invention are the compounds of formula I and their tautomers, pharmaceutically acceptable salts, enantiomeric forms, diastereoisomers and racemates, their use for the inhibition of tumor growth, the preparation of the above-mentioned compounds, medicaments containing them and their manufacture as well as the use of the above-mentioned compounds in the control or prevention of illnesses, especially of cancers such as colorectal, breast, lung, prostate, pancreatic, gastric, bladder, ovarian, melanoma, neuroblastoma, cervical, kidney or renal cancers, leukemias or lymphomas, or in the manufacture of corresponding medicaments.

DETAILED DESCRIPTION OF THE INVENTION

1. Definitions

The term "alkyl" as used herein means a saturated, straight-chain or branched-chain hydrocarbon containing from 1 to 6 carbon atoms, preferably 1 to 4 carbon atoms and more preferably 1 to 3 carbon atoms, such as methyl, ethyl, n-propyl, isopropyl, n-butyl, 2-butyl, t-butyl, n-pentyl, n-hexyl, preferably methyl, ethyl and isopropyl.

The term "halogen" as used herein means fluorine, chlorine and bromine, preferably fluorine or chlorine and more preferably fluorine.

The term "heterocyclyl" as used herein means a saturated, monocyclic ring with 5 to 6 ring atoms which contains up to 3, preferably 1 or 2 heteroatoms selected independently from nitrogen, oxygen or sulfur, and wherein the remaining ring atoms being carbon atoms. Examples of such saturated heterocycles include [1,3]dioxanyl, [1,3]dioxolanyl, pyrrolidinyl, morpholinyl, piperazinyl, piperidinyl, oxazolidinyl, thiazolidinyl, azepanyl and the like, preferably [1,3]dioxanyl or [1,3]dioxolanyl and more preferably [1,3]dioxanyl. Preferably such heterocyclyl groups are unsubstituted.

The term "pyridyl" as used herein means pyrid-2-yl, pyrid-3-yl or pyrid-4-yl, preferably pyrid-2-yl. Such pyridyl is preferably unsubstituted.

As used herein, a "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

2. Detailed Description $R^1$ is fluorine, chlorine, bromine, methyl, methoxy or trifluoromethyl; preferably chlorine, bromine, methoxy or trifluoromethyl and more preferably chlorine, methoxy or trifluoromethyl.

$R^2$ is fluorine, chlorine, bromine, methyl or trifluoromethyl; preferably fluorine, chlorine or trifluoromethyl and more preferably fluorine or chlorine.

Y is N or CH; preferably N.

$R^3$ is a) phenyl, unsubstituted or substituted one to three times by alkyl, preferably once or twice, —OR, —NRR', halogen, —CN, —$CF_3$, —$OCF_3$, —$CHF_2$ or —$OCHF_2$; preferably by alkyl, —OR or halogen (preferably fluorine), b) pyridyl, unsubstituted or substituted one to three times, preferably once or twice, by alkyl; preferably the pyridyl is unsubstituted; or c) heterocyclyl, unsubstituted or substituted one to three times, preferably once or twice, by alkyl; preferably the heterocyclyl is unsubstituted.

R is hydrogen or alkyl; preferably alkyl.

One embodiment of the invention are the compounds of formula I, wherein $R^1$ is chlorine, methoxy or trifluoromethyl;
$R^2$ is fluorine or chlorine;
Y is N;
$R^3$ is a) phenyl, unsubstituted or substituted once or twice, by alkyl, —OR or halogen (preferably fluorine),
b) unsubstituted pyridyl; or
c) unsubstituted heterocyclyl; and
R is alkyl.

Another embodiment of the invention are the compounds of formula I, wherein $R^1$ is chlorine, methoxy or trifluoromethyl; and
$R^2$ is fluorine or chlorine.

Another embodiment of the invention are the compounds of formula I, wherein

Y is N.

Another embodiment of the invention are the compounds of formula I, wherein $R^3$ is a) phenyl, unsubstituted or substituted once or twice by alkyl, —OR, halogen, —CN, —$CF_3$, or —$OCF_3$; or
b) pyridyl, unsubstituted or substituted once or twice by alkyl.

Another embodiment of the invention are the compounds of formula I, wherein $R^3$ is phenyl, unsubstituted or substituted once or twice by alkyl, —OR or halogen.

Another embodiment of the invention are the compounds of formula I, wherein

Y is N; and $R^3$ is phenyl, unsubstituted or substituted once or twice by alkyl, —OR or halogen.

Such compounds, for example, may be selected from the group consisting of:

6-(4-m-Tolyl-piperazin-1-yl)-pyridine-3-sulfonic acid 4-fluoro-2-trifluoromethyl-benzoylamide; sodium salt;
6-(4-Phenyl-piperazin-1-yl)-pyridine-3-sulfonic acid 4-chloro-2-methoxy-benzoylamide; sodium salt;
6-[4-(4-Fluoro-phenyl)-piperazin-1-yl]-pyridine-3-sulfonic acid 4-fluoro-2-trifluoromethyl-benzoylamide; sodium salt;
6-[4-(2-Methoxy-phenyl)-piperazin-1-yl]-pyridine-3-sulfonic acid 4-chloro-2-methoxy-benzoylamide; sodium salt;
6-[4-(4-Methoxy-phenyl)-piperazin-1-yl]-pyridine-3-sulfonic acid 4-chloro-2-trifluoromethyl-benzoylamide; sodium salt;
6-(4-Phenyl-piperazin-1-yl)-pyridine-3-sulfonic acid 2-chloro-4-fluoro-benzoylamide; sodium salt;
6-[4-(4-Fluoro-phenyl)-piperazin-1-yl]-pyridine-3-sulfonic acid 4-chloro-2-methoxy-benzoylamide; sodium salt;
6-[4-(2-Methoxy-phenyl)-piperazin-1-yl]-pyridine-3-sulfonic acid 4-chloro-2-trifluoromethyl-benzoylamide; sodium salt;
6-[4-(2-Methoxy-phenyl)-piperazin-1-yl]-pyridine-3-sulfonic acid 2-chloro-4-fluoro-benzoylamide; sodium salt;
6-(4-Phenyl-piperazin-1-yl)-pyridine-3-sulfonic acid 2,4-dichloro-benzoylamide; sodium salt;
6-[4-(4-Fluoro-phenyl)-piperazin-1-yl]-pyridine-3-sulfonic acid 2,4-dichloro-benzoylamide; sodium salt;
6-[4-(4-Fluoro-phenyl)-piperazin-1-yl]-pyridine-3-sulfonic acid 2-chloro-4-fluoro-benzoylamide; sodium salt;
6-(4-Phenyl-piperazin-1-yl)-pyridine-3-sulfonic acid 4-fluoro-2-trifluoromethyl-benzoylamide; sodium salt;
6-[4-(2-Fluoro-phenyl)-piperazin-1-yl]-pyridine-3-sulfonic acid 4-fluoro-2-trifluoromethyl-benzoylamide; sodium salt; and
6-[4-(2,4-Difluoro-phenyl)-piperazin-1-yl]-pyridine-3-sulfonic acid 4-fluoro-2-trifluoromethyl-benzoylamide; sodium salt.

Another embodiment of the invention are the compounds of formula I, wherein $R^3$ is unsubstituted pyridyl.

Another embodiment of the invention are the compounds of formula I, wherein

Y is N; and
$R^3$ is unsubstituted pyridyl.

Such compounds, for example, may be selected from the group consisting of:

6-(4-Pyridin-2-yl-piperazin-1-yl)-pyridine-3-sulfonic acid 2,4-dichloro-benzoylamide; sodium salt;
6-(4-Pyridin-2-yl-piperazin-1-yl)-pyridine-3-sulfonic acid 2-chloro-4-fluoro-benzoylamide; sodium salt; and
6-(4-Pyridin-2-yl-piperazin-1-yl)-pyridine-3-sulfonic acid 4-fluoro-2-trifluoromethyl-benzoylamide; sodium salt.

Another embodiment of the invention are the compounds of formula I, wherein

Y is CH.

Another embodiment of the invention are the compounds of formula I, wherein $R^3$ is unsubstituted heterocyclyl.

Another embodiment of the invention are the compounds of formula I, wherein

Y is CH; and
$R^3$ is unsubstituted heterocyclyl.

Such compounds, for example, may be selected from the group consisting of:

6-(1,5-Dioxa-9-aza-spiro[5.5]undec-9-yl)-pyridine-3-sulfonic acid 4-chloro-2-trifluoromethyl-benzoylamide; sodium salt; and 6-(1,5-Dioxa-9-aza-spiro[5.5]undec-9-yl)-pyridine-3-sulfonic acid 4-chloro-2-methoxy-benzoylamide; sodium salt.

One embodiment of the invention is a process for the preparation of the compounds of formula I, by reacting a compound of formula V,

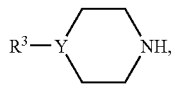

formula V wherein $R^3$ has the significance given for formula I, with a compound of formula IV,

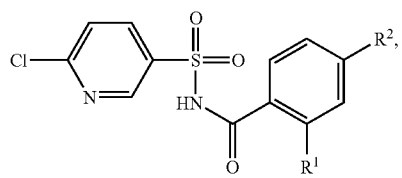

formula IV wherein $R^1$ and $R^2$ have the significance given for formula I, to give the compounds of formula I,

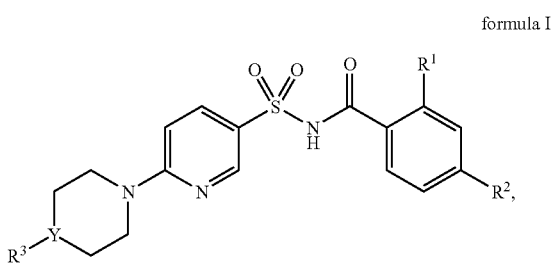

formula I wherein $R^1$, $R^2$ and $R^3$ have the significance given for formula I.

The compounds of formula I, or a pharmaceutically acceptable salt thereof, which are subject of the present invention, may be prepared by any process known to be applicable to the preparation of chemically-related compounds. Such processes, when used to prepare a compound of the formula I, or a pharmaceutically-acceptable salt thereof, are illustrated by the following representative schemes 1 and 2 (and the examples) in which, unless otherwise stated, R, $R^1$, $R^2$ and $R^3$ have the significance given herein before for formula I. Necessary starting materials are either commercially available or they may be obtained by standard procedures of organic chemistry. The preparation of such starting materials is e.g. described within the accompanying examples or in the literature cited below with respect to scheme 1. Alternatively necessary starting materials are obtainable by analogous procedures to those illustrated which are within the ordinary skill of an organic chemist.

Scheme 1:

The compounds of the present invention can be prepared according to scheme 1 and are named I:

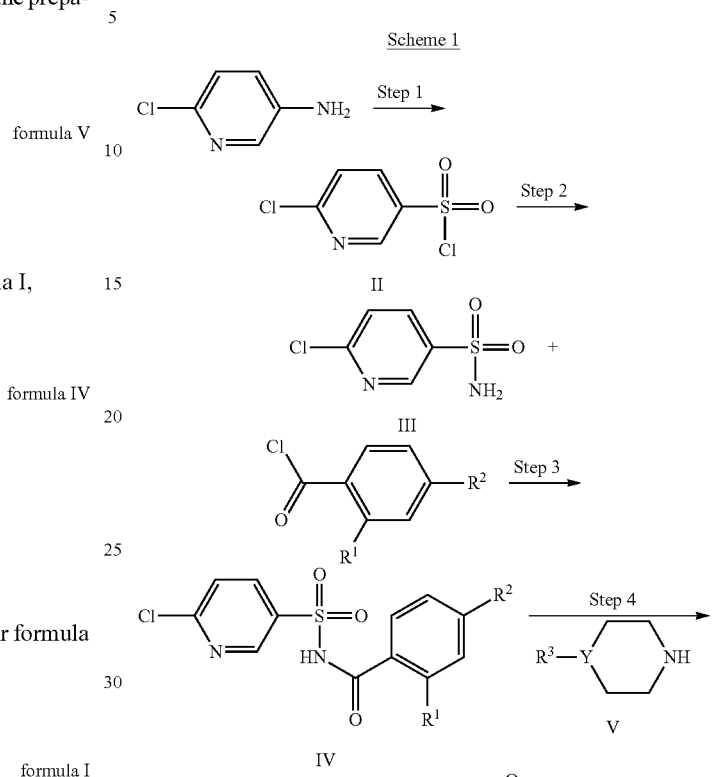

In scheme 1, $R^1$, $R^2$, $R^3$ and Y have the significance given above for formula I.

Step 1:

Step 1 of the reaction sequence (scheme 1) is a one step process in which an aminopyridine is converted into a pyridine sulfonyl chloride using methods well known to someone skilled in the art, e.g. diazotization followed by nucleophilic displacement. This reaction is typically carried out with solvents such as acetic acid, sulphuric acid, hydrochloric acid, water and mixtures thereof, at temperatures between −78° C. and 100° C.

Step 2:

Step 2 of the reaction sequence (scheme 1) is a one step process in which a pyridine sulfonyl chloride is converted into a pyridine sulfonamide using methods well known to someone skilled in the art, e.g. ammonolysis. The reaction is typically carried out with solvents such as dichloromethane, dichloroethane, acetonitrile, dioxane, tetrahydrofuran, dimethylformamide and mixtures thereof, at temperatures between −78° C. and 30° C.

Step 3:

Step 3 of the reaction sequence (scheme 1) is a one step process in which acylation of III gives the acylsulfonamide derivatives of formula IV using methods well known to someone skilled in the art. The reaction is typically carried out in solvents such as dichloromethane, dichloroethane, acetonitrile, dioxane, tetrahydrofuran, chloroform, dimethylformamide and mixtures thereof, at temperatures between −10° C. and 100° C. Typically used bases are sodium hydride, potassium hydride, potassium carbonate, triethylamine, diisopropylethylamine, and 1,8-diazabicyclo[5.4.0]undec-7-ene.

Step 4:

Step 4 of the reaction sequence (scheme 1) is a one step process in which a 2-chloropyridine sulphonamide of formula IV is converted by reaction with a 2-piperidine or 2-piperazine derivative of formula V into a 2-piperidine- or 2-piperazine-pyridine sulphonamide of formula I using methods well known to someone skilled in the art. The reaction is typically carried out with or without solvents such as dichloromethane, dichloroethane, tetrahydrofuran, dioxane and mixtures thereof, at temperatures between 0° C. and 100° C. The reactions are carried out with or without bases, typical bases used are sodium hydride, potassium hydride, potassium carbonate, triethylamine, diisopropylethylamine, and (1,8-diazabicyclo[5.4.0]undec-7-ene.

The compounds of formula I can contain one or several chiral centers and can then be present in a racemic, a enantiomeric or diastereomeric form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Pharmaceutical composition or medicaments containing a compound of the present invention or a pharmaceutically acceptable salt thereof and a pharmaceutically acceptable carrier are an object of the present invention, as is a process for their production, which comprises bringing one or more compounds of the present invention and/or pharmaceutically acceptable salts and, if desired, one or more other therapeutically valuable substances into a galenical administration form together with one or more pharmaceutically acceptable carriers.

An embodiment of the invention is a pharmaceutical composition, containing one or more compounds according to formula I, together with pharmaceutically acceptable carriers.

Another embodiment of the invention is a pharmaceutical composition, containing one or more compounds according to formula I, for the inhibition of tumor growth.

Another embodiment of the invention is a pharmaceutical composition, containing one or more compounds according to formula I, for the treatment of cancer.

Another embodiment of the invention is a pharmaceutical composition containing one or more compounds of formula I as active ingredients together with pharmaceutically acceptable carriers for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of corresponding pharmaceutical compositions for the inhibition of tumor growth.

CellTiter-Glo™ Assay in HCT 116 Cells

The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCl-247) were cultivated in RPMI 1640 medium with GlutaMAX™ I (Invitrogen, Cat-No. 61870-010), 5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells were seeded in 384 well plates, 1000 cells per well, in the same medium. The next day the test compounds were added in various concentrations ranging from 30 µM to 0.0015 µM (10 concentrations, 1:3 diluted). After 5 days the CellTiter-Glo™ assay was done according to the instructions of the manufacturer (CellTiter-Glo™ Luminescent Cell Viability Assay, from Promega). In brief the cell-plate was equilibrated to room temperature for approximately 30 minutes and than the CellTiter-Glo™ reagent was added. The contents were carefully mixed for 15 minutes to induce cell lysis. After 45 minutes the luminescent signal was measured in Victor 2, (scanning multiwell spectrophotometer, Wallac).

Details:

1st Day:
  Medium: RPMI 1640 with GlutaMAX™ I (Invitrogen, Cat-Nr. 61870), 5% FCS (Sigma Cat.-No. F4135), Pen/Strep (Invitrogen, Cat No. 15140).
  HCT116 (ATCC-No. CCl-247): 1000 cells in 60 µl per well of 384 well plate (Greiner 781098, µClear-plate white)
  After seeding incubate plates 24 h at 37° C., 5% $CO_2$ 2nd. Day: Induction (Treatment with Compounds, 10 Concentrations):
  In order to achieve a final concentration of 30 µM as highest concentration 3.5 µl of 10 mM compound stock solution were added directly to 163 µl media. Then step e) of the dilution procedure described below, was followed.
  In order to achieve the second highest to the lowest concentrations, a serial dilution with dilution steps of 1:3 was followed according to the procedure (a-e) as described here below:

a) for the second highest concentration add 10 µl of 10 mM stock solution of compound to 20 µl dimethylsulfoxide (DMSO)

b) dilute 8×1:3 (always 10 µl to 20 µl DMSO) in this DMSO dilution row (results in 9 wells with concentrations from 3333.3 µM to 0.51 µM)

c) dilute each concentration 1: 47.6 (3.5 µl compound dilution to 163 µl media)

e) add 10 µl of every concentration to 60 µl media in the cell plate resulting in final concentration of DMSO: 0.3% in every well and resulting in 10 final concentration of compounds ranging from 30 µM to 0.0015 µM.
  Each compound is tested in triplicate.
  Incubate 120 h (5 days) at 37° C., 5% $CO_2$ Analysis:
  Add 30 µl CellTiter-Glo™ Reagent per well,
  shake 15 minutes at room temperature
  incubate further 45 minutes at room temperature without shaking Measurement:
  Victor 2 scanning multiwell spectrophotometer (Wallac), Luminescence mode (0.5 sec/read, 477 nm)
  Determine IC50 using a non-linear curve fit (XLfit software (ID Business Solution Ltd., Guilford, Surrey, UK))

With all compounds a significant inhibition of HCT 116 cell viability was detected, which is exemplified by the compounds shown in Table 1.

TABLE 1

| Results: | |
|---|---|
| Examples | IC50 HCT 116 [µM] |
| 1-1 | 3.35 |
| 1-2 | 4.28 |
| 1-11 | 1.25 |
| 1-3, 1-4, 1-5, 1-6, 1-7, 1-8, 1-9, 1-10, | 1.00-10.00 |

TABLE 1-continued

Results:

| Examples | IC50 HCT 116 [µM] |
|---|---|
| 1-12, 1-13, 1-14, 1-15, 1-16, 1-17, 1-18, 1-19, 1-20 | |

The compounds according to this invention and their pharmaceutically acceptable salts can be used as medicaments, e.g. in the form of pharmaceutical compositions.

The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically acceptable, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:
1. Mix items 1, 2 and 3 in a suitable mixer for 30 minutes.
2. Add items 4 and 5 and mix for 3 minutes.
3. Fill into a suitable capsule.

The following examples are provided to aid the understanding of the present invention, the true scope of which is set forth in the appended claims. It is understood that modifications can be made in the procedures set forth without departing from the spirit of the invention.

Experimental Procedures

General Procedure for the Preparation of the Pyridine Sulfonic Acid Amide Material 6-Chloro-pyridine-3-sulfonyl Chloride Sodium nitrite (3.45 g, 0.05 mol) was added portion wise to a stirred solution of 6-chloro-pyridin-3-ylamine (6.4 g, 0.05 mol) in acetic acid (56 ml) and HCl (conc) (9.92 ml) while maintaining the temperature below 15° C. This solution was then added drop wise to a stirred solution of sulfur dioxide (17.2 g, 0.27 mol), copper (II) chloride (1.85 g, 0.011 mol) and water (2.2 ml) in acetic acid (37 ml) at 5° C. The reaction mixture was allowed to warm to room temperature and poured over ice water and stirred for a further 15 min. The resultant precipitate was collected by filtration, washed with water and dried overnight in a vacuum oven to give 6-chloro-pyridine-3-sulfonyl chloride (6.41 g, 60.5% yield); (400 MHz; $d^6$-DMSO) 8.54 (1H, d), 7.96 (1H, dd), 7.50 (1H, d).

6-Chloro-pyridine-3-sulfonic Acid Amide

6-Chloro-pyridine-3-sulfonyl chloride (5.0 g, 0.024 mol) was dissolved in a 0.5M solution of ammonia in dioxane (125 mL) at −5° C. The mixture was allowed to warm to room temperature and the mixture stirred for 1 hour. The mixture was filtered through Celite®, washed twice with dioxane and concentrated in vacuo to afford 6-chloro-pyridine-3-sulfonic acid amide as an off white solid 4.55 g (98% yield). LC @UV215 nm; Rt 1.05: 100%, m/z (ES+): 193/195 (400 MHz; $d^6$-DMSO) 8.79 (1H, d), 8.21 (1H, dd), 7.75 (1H, d) 7.70 (2H, br S)

6-Chloro-pyridine-3-sulfonic acid 2,4-dichloro-benzoylamide Sodium Salt

Sodium hydride (60% v dispersion in mineral oil, 2.5 g, 0.062 mol) was added portion wise to a suspension of 6-chloro-pyridine-3-sulfonic acid amide (4 g, 0.0207 mol) in dioxane (75 ml) at 0° C. and the whole was stirred for 1 hour. A solution of 2,4-dichloro-benzoyl chloride (5.2 g, 0.0248 mol) in dioxane (75 ml) was added drop wise at 0° C. and the reaction mixture stirred at room temperature for 3 hours. The mixture was filtered under vacuum and the resultant solid washed twice with dioxane (200 ml). This solid was then dissolved in hot acetonitrile (150 ml). The acetonitrile was dried ($MgSO_4$) and concentrated to give the sulphonamide as a white solid 6.7 g, (88% yield). LC @UV215 nm; Rt 1.92: 98%, m/z (ES+): 365/367

(M+H); $\delta_H$ (400 MHz; $d^6$-DMSO) 8.65 (1H, d), 8.10 (1H, dd), 7.50 (1H, d), 7.41-7.38 (2H, m), 7.25 (1H, dd), Final Products Sodium Salt Formation Depending on the work-up procedure i.e. the HPLC purification conditions, the final products described below (in Examples 1-1 to 1-20) were obtained either directly as sulfonamide sodium salts (neutral HPLC-conditions—e.g. aqueous eluent is water (pH is 7)/acetonitrile 9:1 and the organic eluent is acetonitrile) or they were obtained firstly as sulfonamide ammonium salts (basic HPLC conditions—e.g. with ammonium carbonate as buffer pH=10) or as sulfonamides in their salt free form (acidic HPLC conditions—e.g. the aqueous eluent is water with 0.2% acetic acid and the organic eluent is acetonitrile with 0.2% acetic acid)

These obtained sulfonamides or sulfonamide ammonium salts were or are converted to their sodium salts using the following procedure:

To a solution of the sulfonamide or sulfonamide ammonium salt (1 eq., e.g. 1 mmol) in tetrahydrofuran (e.g. 10 ml), 1 eq. (e.g. 1 mmol) sodium methoxide (25% solution in methanol) is added and the mixture is stirred at room temperature for 1 hour. The tetrahydrofuran is removed in vacuo and the residue suspended in diethyl ether (e.g. 50 to 100 ml) and heated to reflux four 1 hour, cooled down to room temperature filtered off and dried.

EXAMPLE 1-1

6-(4-Pyridin-2-yl-piperazin-1-yl)-pyridine-3-sulfonic acid 2,4-dichloro-benzoylamide; ammonium salt Triethylamine (26 µl, 0.18 mmol) and 1-pyridin-2-yl-piperazine (82 mg, 0.5 mmol) was added to a stirred solution of 6-chloro-pyridine-3-sulfonic acid 2,4-dichloro-benzoylamide sodium salt (70 mg, 0.18 mmol) in dioxane at room temperature. The reaction mixture was then heated to 80° C. for 48 hours. The reaction mixture was concentrated in vacuo and the crude solid dissolved in acetonitrile water (1:1, 1.5 ml) and purified by preparative HPLC (basic HPLC conditions with ammonium carbonate as buffer pH=10) to give the final compound, MS (ESI+): 492/494 (M+H).

$^1$H-NMR (500 MHz, D$_6$-DMSO): 3.66 (t, 4H), 3.84 (t, 4H), 6.69 (m, 1H), 6.88 (d, 1H), 7.00 (d, 1H), 7.49 (m, 2H), 7.58 (m, 1H), 7.67 (s, 1H), 7.97 (m, 1H), 8.15 (d, 1H), 8.62 (d, 1H)

EXAMPLE 1-2 to 1-20

The following examples were prepared in an analogous manner as described for example 1-1, using the appropriate starting material:

| Example No. | Systematic Name | $^1$H-NMR (500 MHz, D$_6$-DMSO) |
|---|---|---|
| 1-2 | 6-(1,5-Dioxa-9-aza-spiro[5.5]undec-9-yl)-pyridine-3-sulfonic acid 4-chloro-2-trifluoromethyl-benzoylamide; ammonium salt | 1.65 (m, 2H), 1.86 (m, 4H), 3.70 (t, 4H), 3.88 (t, 4H), 6.98 (d, 1H), 7.61 (d, 1H), 7.81 (d, 1H), 7.86 (s, 1H), 7.91 (d, 1H), 8.56 (d, 1H) |
| 1-3 | 6-(4-m-Tolyl-piperazin-1-yl)-pyridine-3-sulfonic acid 4-fluoro-2-trifluoromethyl-benzoylamide; sodium salt | 2.18 (s, 3H), 4 H under solvent, 3.76 (m, 4H), 6.55 (d, 1H), 6.70 (dd, 1H), 6.72 (d, 1H), 6.94 (d, 1H), 7.03 (t, 1H), 7.51 (dt, 1H), 7.59 (m, 2H), 7.86 (dd, 1H), 8.52 (d, 1H) |
| 1-4 | 6-(4-Phenyl-piperazin-1-yl)-pyridine-3-sulfonic acid 4-chloro-2-methoxy-benzoylamide | 4H under solvent, 3.85 (m, 4H), 3.86 (s, 3H), 6.82 (t, 1H), 7.00 (d, 2H), 7.03 (d, 1H), 7.06 (d, 1H), 7.24 (m, 3H), 7.42 (d, 1H), 7.96 (dd, 1H), 8.62 (d, 1H) |
| 1-5 | 6-(4-Pyridin-2-yl-piperazin-1-yl)-pyridine-3-sulfonic acid 2-chloro-4-fluoro-benzoylamide; ammonium salt | 3.63 (m, 4H), 3.80 (m, 4H), 6.65 (m, 1H), 6.85 (d, 1H), 6.96 (d, 1H), 7.22 (m, 1H), 7.43 (m, 1H), 7.55 (m, 2H), 7.95 (dd, 1H), 8.13 (dd, 1H), 8.59 (d, 1H) |
| 1-6 | 6-(4-Pyridin-2-yl-piperazin-1-yl)-pyridine-3-sulfonic acid 4-fluoro-2-trifluoromethyl-benzoylamide; ammonium salt | 3.41 (m, 4H), 3.60 (m, 4H), 6.44 (dd, 1H), 6.64 (d, 1H), 6.76 (d, 1H), 7.35 (m, 2H), 7.44 (m, 2H), 7.72 (dd, 1H), 7.90 (dd, 1H), 8.37 (d, 1H) |
| 1-7 | 6-[4-(4-Fluoro-phenyl)-piperazin-1-yl]-pyridine-3-sulfonic acid 4-fluoro-2-trifluoromethyl-benzoylamide; ammonium salt | 4H under solvent, 3.64 (m, 4H), 6.83 (m, 5H), 7.39 (m, 1H), 7.48 (m, 2H), 7.74 (dd, 1H), 8.39 (d, 1H) |
| 1-8 | 6-[4-(2-Methoxy-phenyl)-piperazin-1-yl]-pyridine-3-sulfonic acid 4-chloro-2-methoxy-benzoylamide; ammonium salt | 2.83 (m, 4H), 3.59 (s, 3H), 3.60 (m, 4H), 3.63 (s, 3H), 6.73 (m, 5H), 6.83 (dd, 1H), 6.99 (d, 1H), 7.20 (d, 1H), 7.72 (dd, 1H), 8.38 (d, 1H) |
| 1-9 | 6-[4-(4-Methoxy-phenyl)-piperazin-1-yl]-pyridine-3-sulfonic acid 4-chloro-2-trifluoromethyl-benzoylamide | 3.13 (m, 4H), 3.70 (s, 3H), 3.86 (m, 4H), 6.86 (d, 2H), 6.97 (d, 2H), 7.04 (d, 1H), 7.62 (d, 1H), 7.83 (d, 1H), 7.89 (s, 1H), 7.95 (dd, 1H), 8.60 (d, 1H) |
| 1-10 | 6-(4-Phenyl-piperazin-1-yl)-pyridine-3-sulfonic acid 2-chloro-4-fluoro-benzoylamide | 4 H under solvent, 3.86 (m, 4H), 6.82 (m, 1H), 6.99 (d, 2H), 7.04 (d, 1H), 7.26 (m, 3H), 7.52 (d, 1H), 7.57 (m, 1H), 7.97 (dd, 1H), 8.63 (d, 1H) |
| 1-11 | 6-[4-(4-Fluoro-phenyl)-piperazin-1-yl]-pyridine-3-sulfonic acid 4-chloro-2-methoxy-benzoylamide | 3.20 (m, 4H), 3.85 (m, 7H), 7.05 (m, 6H), 7.22 (s, 1H), 7.43 (d, 1H), 7.96 (dd, 1H), 8.61 (m, 1H) |
| 1-12 | 6-(1,5-Dioxa-9-aza-spiro[5.5]undec-9-yl)-pyridine-3-sulfonic acid 4-chloro-2-methoxy-benzoylamide | 1.65 (m, 2H), 1.86 (m, 4H), 3.69 (m, 4H), 3.87 (m, 7H), 6.98 (d, 1H), 7.06 (d, 1H), 7.22 (s, 1H), 7.42 (d, 1H), 7.91 (dd, 1H), 8.57 (m, 1H) |
| 1-13 | 6-[4-(2-Methoxy-phenyl)-piperazin-1-yl]-pyridine-3-sulfonic acid 4-chloro-2-trifluoromethyl-benzoylamide | 3.06 (m, 4H), 3.82 (s, 3H), 3.84 (m, 4H), 6.87-7.05 (m, 5H), 7.63 (d, 1H), 7.83 (d, 1H), 7.89 (s, 1H), 7.95 (dd, 1H), 8.60 (m, 1H) |
| 1-14 | 6-[4-(2-Methoxy-phenyl)-piperazin-1-yl]-pyridine-3-sulfonic acid 2-chloro-4-fluoro-benzoylamide; sodium salt | 3.07 (m, 4H), 3.82 (s, 3H), 3.84 (m, 4H), 6.87-7.06 (m, 5H), 7.29 (m, 1H), 7.52 (m, 1H), 7.57 (m, 1H), 7.97 (m, 1H), 8.62 (m, 1H) |
| 1-15 | 6-(4-Phenyl-piperazin-1-yl)-pyridine-3-sulfonic acid 2,4-dichloro-benzoylamide; sodium salt | 4H under solvent, 3.86 (m, 4H), 6.82 (m, 1H), 7.01 (m, 3H), 7.25 (m, 2H), 7.50 (m, 2H), 7.69 (s, 1H), 7.97 (dd, 1H), 8.62 (m, 1H) |
| 1-16 | 6-[4-(4-Fluoro-phenyl)-piperazin-1-yl]-pyridine-3-sulfonic acid 2,4-dichloro-benzoylamide; sodium salt | 3.19 (m, 4H), 3.85 (m, 4H), 7.05 (m, 5H), 7.50 (m, 2H), 7.69 (s, 1H), 7.97 (dd, 1H), 8.62 (m, 1H) |
| 1-17 | 6-[4-(4-Fluoro-phenyl)-piperazin-1-yl]-pyridine-3-sulfonic acid 2-chloro-4-fluoro-benzoylamide; sodium salt | 3.20 (m, 4H), 3.85 (m, 4H), 6.99-7.11 (m, 5H), 7.28 (m, 1H), 7.51 (d, 1H), 7.56 (m, 1H), 7.97 (m, 1H), 8.62 (dd, 1H) |
| 1-18 | 6-(4-Phenyl-piperazin-1-yl)-pyridine-3-sulfonic acid 4-fluoro-2-trifluoromethyl-benzoylamide; sodium salt | 4 H under solvent, 3.87 (m, 4H), 6.82 (m, 1H), 6.99 (d, 2H), 7.04 (d, 1H), 7.25 (m, 2H), 7.60 (m, 1H), 7.68 (m, 1H), 7.72 (m, 1H), 7.96 (dd, 1H), 8.61 (m, 1H) |

-continued

| Example No. | Systematic Name | ¹H-NMR (500 MHz, D₆-DMSO) |
|---|---|---|
| 1-19 | 6-[4-(2-Fluoro-phenyl)-piperazin-1-yl]-pyridine-3-sulfonic acid 4-fluoro-2-trifluoromethyl-benzoylamide; sodium salt | 3.13 (m, 4H), 3.88 (m, 4H), 6.99-7.20 (m, 5H), 7.61 (m, 1H), 7.68 (m, 1H), 7.73 (m, 1H), 7.96 (dd, 1H), 8.61 (m, 1H) |
| 1-20 | 6-[4-(2,4-Difluoro-phenyl)-piperazin-1-yl]-pyridine-3-sulfonic acid 4-fluoro-2-trifluoromethyl-benzoylamide; sodium salt | 3.07 (m, 4H), 3.87 (m, 4H), 7.03 (m, 2H), 7.13 (m, 1H), 7.22 (m, 1H), 7.61 (m, 1H), 7.68 (m, 1H), 7.72 (m, 1H), 7.96 (dd, 1H), 8.61 (m, 1H) |

The invention claimed is:

1. A compound according to formula I,

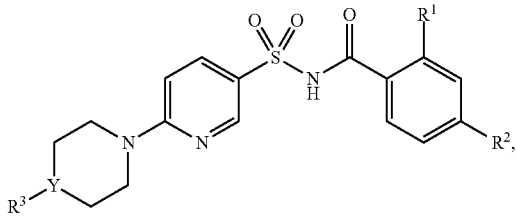

formula I wherein

R¹ is selected from the group consisting of: fluorine, chlorine, bromine, methyl, methoxy and trifluoromethyl;

R² is selected from the group consisting of: fluorine, chlorine, bromine, methyl and trifluoromethyl;

Y is N or CH;

R³ is selected from the group consisting of:
  a) phenyl, unsubstituted or substituted one to three times by alkyl, —OR, —NRR', halogen, —CN, —CF₃, —OCF₃, —CHF₂ or —OCHF₂;
  b) pyridyl, unsubstituted or substituted one to three times by alkyl; and
  c) heterocyclyl, unsubstituted or substituted one to three times by alkyl;

and

R is hydrogen or alkyl; or a pharmaceutically acceptable salt thereof.

2. A compound according to claim 1, wherein

R¹ is selected from the group consisting of: chlorine, methoxy and trifluoromethyl; and R² is fluorine or chlorine.

3. A compound according to claim 1, wherein

Y is N.

4. A compound according to claim 1, wherein Y is CH.

5. A compound selected from the group consisting of:

6-(4-m-Tolyl-piperazin-1-yl)-pyridine-3-sulfonic acid 4-fluoro-2-trifluoromethyl-benzoylamide; sodium salt;

6-(4-Phenyl-piperazin-1-yl)-pyridine-3-sulfonic acid 4-chloro-2-methoxy-benzoylamide; sodium salt;

6-[4-(4-Fluoro-phenyl)-piperazin-1-yl]-pyridine-3-sulfonic acid 4-fluoro-2-trifluoromethyl-benzoylamide; sodium salt;

6-[4-(2-Methoxy-phenyl)-piperazin-1-yl]-pyridine-3-sulfonic acid 4-chloro-2-methoxy-benzoylamide; sodium salt;

6-[4-(4-Methoxy-phenyl)-piperazin-1-yl]-pyridine-3-sulfonic acid 4-chloro-2-trifluoromethyl-benzoylamide; sodium salt;

6-(4-Phenyl-piperazin-1-yl)-pyridine-3-sulfonic acid 2-chloro-4-fluoro-benzoylamide; sodium salt;

6-[4-(4-Fluoro-phenyl)-piperazin-1-yl]-pyridine-3-sulfonic acid 4-chloro-2-methoxy-benzoylamide; sodium salt;

6-[4-(2-Methoxy-phenyl)-piperazin-1-yl]-pyridine-3-sulfonic acid 4-chloro-2-trifluoromethyl-benzoylamide; sodium salt;

6-[4-(2-Methoxy-phenyl)-piperazin-1-yl]-pyridine-3-sulfonic acid 2-chloro-4-fluoro-benzoylamide; sodium salt;

6-(4-Phenyl-piperazin-1-yl)-pyridine-3-sulfonic acid 2,4-dichloro-benzoylamide; sodium salt;

6-[4-(4-Fluoro-phenyl)-piperazin-1-yl]-pyridine-3-sulfonic acid 2,4-dichloro-benzoylamide; sodium salt;

6-[4-(4-Fluoro-phenyl)-piperazin-1-yl]-pyridine-3-sulfonic acid 2-chloro-4-fluoro-benzoylamide; sodium salt;

6-(4-Phenyl-piperazin-1-yl)-pyridine-3-sulfonic acid 4-fluoro-2-trifluoromethyl-benzoylamide; sodium salt;

6-[4-(2-Fluoro-phenyl)-piperazin-1-yl]-pyridine-3-sulfonic acid 4-fluoro-2-trifluoromethyl-benzoylamide; sodium salt;

6-[4-(2,4-Difluoro-phenyl)-piperazin-1-yl]-pyridine-3-sulfonic acid 4-fluoro-2-trifluoromethyl-benzoylamide; sodium salt;

6-(4-Pyridin-2-yl-piperazin-1-yl)-pyridine-3-sulfonic acid 2,4-dichloro-benzoylamide; sodium salt;

6-(4-Pyridin-2-yl-piperazin-1-yl)-pyridine-3-sulfonic acid 2-chloro-4-fluoro-benzoylamide; sodium salt;

6-(4-Pyridin-2-yl-piperazin-1-yl)-pyridine-3-sulfonic acid 4-fluoro-2-trifluoromethyl-benzoylamide; sodium salt;

6-(1,5-Dioxa-9-aza-spiro[5.5]undec-9-yl)-pyridine-3-sulfonic acid 4-chloro-2-trifluoromethyl-benzoylamide; sodium salt; and 6-(1,5-Dioxa-9-aza-spiro[5.5]undec-9-yl)-pyridine-3-sulfonic acid 4-chloro-2-methoxy-benzoylamide; sodium salt.

6. A pharmaceutical composition comprising a compound according to claim 1 and a, pharmaceutically acceptable carrier.

7. A process for the preparation of a compound according to claim 1, said process comprising:

reacting a compound of formula V,

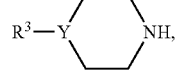

formula V wherein $R^3$ and Y have the same significance given in claim 1, with a compound of formula IV,
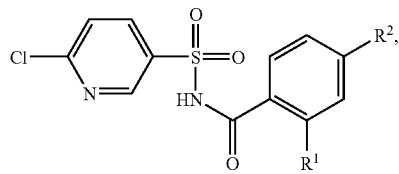
formula IV
wherein $R^1$ and $R^2$ have the same significance given in claim 1, to produce a compound according to formula I,
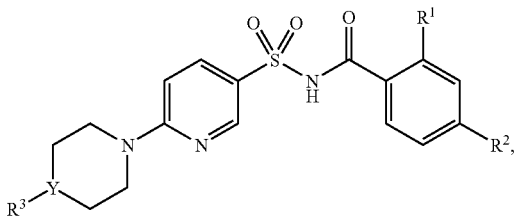
formula I
wherein $R^1$, $R^2$ and $R^3$ have the same significance given in claim 1.
* * * * *